United States Patent [19]

Jones

[11] 4,278,081
[45] Jul. 14, 1981

[54] TRACHEAL TUBE

[76] Inventor: James W. Jones, 4108 James Dr., Metairie, La. 70003

[21] Appl. No.: 879,078

[22] Filed: Feb. 21, 1978

[51] Int. Cl.$^3$ .......................................... A61M 16/00
[52] U.S. Cl. ............................................. 128/207.15
[58] Field of Search .................. 128/208, 348, 349 B, 128/349 BV, 350 R, 350 V, 351, DIG. 29, DIG. 26, 140 R, 140 N, 145.5, 207.14, 207.15, 207.17

[56] References Cited

U.S. PATENT DOCUMENTS

| | | | |
|---|---|---|---|
| 2,908,269 | 10/1959 | Cheng | 128/351 |
| 2,923,299 | 2/1960 | Blackwood | 128/351 |
| 3,769,983 | 11/1973 | Merav | 128/351 |
| 3,788,326 | 1/1974 | Jacobs | 128/351 |
| 4,009,720 | 3/1977 | Crandall | 128/351 |

FOREIGN PATENT DOCUMENTS

| | | | |
|---|---|---|---|
| 933307 | 8/1963 | United Kingdom | 128/351 |
| 1153863 | 5/1969 | United Kingdom | 128/351 |

OTHER PUBLICATIONS

*The Laryngoscope,* "The K. E. P. Laryngeal-Tracheal Stent", pp. 271-275, Passy et al., 3-18-71.

*Primary Examiner*—C. Fred Rosenbaum
*Attorney, Agent, or Firm*—Keaty & Garvey

[57] ABSTRACT

A self inflating and self deflating tracheal tube is comprised generally of an elongated air conveying tube having a cuff at the distal end portion thereof, the cuff forming a fluid tight seal with the tracheal wall during inhalation of the patient. Enlarged openings in the tube wall adjacent and into the tracheal cuff form a path of lesser resistance for air flowing through the tube from its proximal to its distal end. During exhalation of the patient, air within the cuff is quickly and firstly discharged into the tube before or substantially simultaneous with the exit of air from the lungs and trachea of the patient. A flange for attachment of the tube to the neck portion of a patient is provided which flanged portion is adjustable with respect to the tube allowing the surgeon to properly fit and compensate for changes in the size of the individual patient's anatomy. There is further provided an obturator which is placeable by the surgeon into the trachea of the patient before insertion of the tube and flange structure. The obturator can be provided with a gripping surface for the attachment of the surgeon's finger or hand thereto facilitating easy insertion. The obturator forms a substantially fluid tight seal with the wall portions of the trachea above the portion of the trachea through which the tracheal tube enters, thus negating the flow of fluids (including gaseous and liquid fluids such as stomach acids and the like) from the esophagus into the trachea.

32 Claims, 11 Drawing Figures

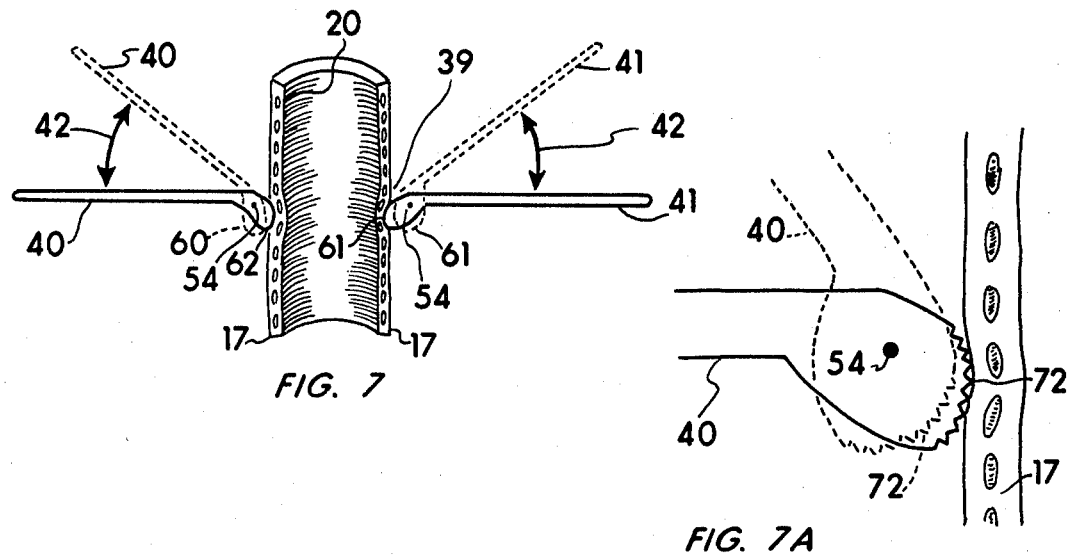
FIG. 7
FIG. 7A
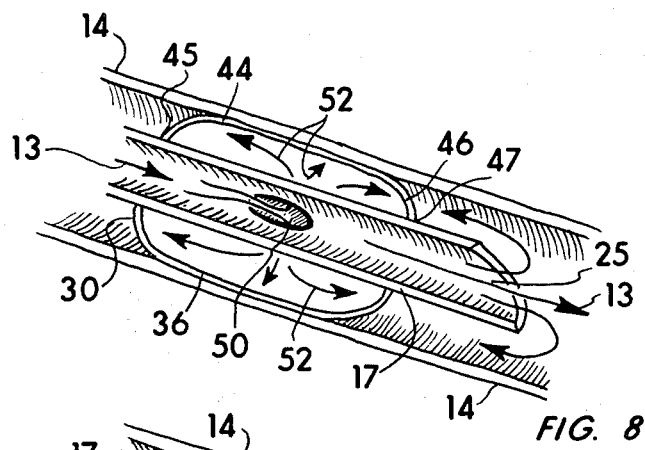
FIG. 8
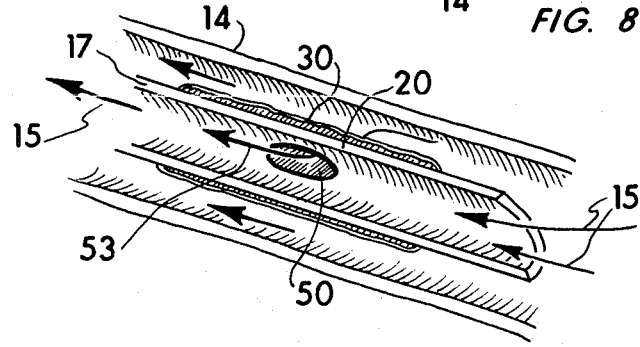
FIG. 9
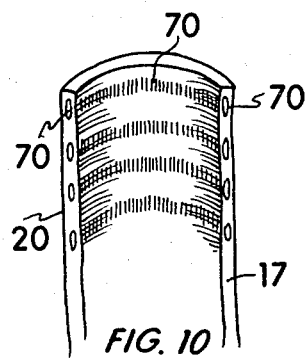
FIG. 10

TRACHEAL TUBE

BACKGROUND OF THE INVENTION

1. Field of the Invention

The present invention relates to medical instruments and more particularly relates to the trachael tube having a self-inflating and self-deflating trachael cuff portion. Even more particularly, the present invention relates to an endotrachael or tracheotomy tube having a cuff portion which seals off the flow of fluids other than through the tube itself during inhalation of the patient, the cuff self-deflating during exhalation of the patient, withdrawing any contact with the trachael wall.

2. General Background and Prior Art

Tubes are utilized often by surgeons to ventilate a patient's lungs. These tubes generally are of two types depending on their structure and use. The first type of tube is referred to generally as an "endotracheal" tube. An endotracheal tube requires generally that insertion of the tube be through an upper airway, such as the mouth, nose or trachea. The use of an endotracheal tube does not contemplate an incision into the trachea of the patient for its insertion.

A second type of tracheal tube is called a tracheostomy tube and requires that an incision be made in the neck region at the base of the throat and extending into the inner wall of the trachea. A tracheotomy thus allows insertion of the tube through the trachea wall rather than an upper airway in order to properly ventilate the lungs.

In the case of either an endotracheal tube or a tracheostomy tube, both tubes generally utilize a "cuff" which is a structure provided at the generally distal end portion of the tube. The cuff functions as a sealing member which inflates or is inflated in order to form a seal between the tube and the wall of the trachea. Thus, during ventilation of the patient, only air flow through the center of the tube occurs thereby negating the chance for inadvertent and undesireable escape of air from the lungs. If the tube is then connected to a ventilating apparatus or resuscitator, the flow of air will be governed by the resuscitator since a seal will have been perfected with the wall of the trachea.

A further use for the cuff portion of the endotracheal or tracheostomy tube is seen. This is the isolation of the flow of fluids between the respiratory organs of the individual patient and the stomach and esophagus. It is essential that the stomach and esophagus be separated from the respiratory organs in order to prevent the inadvertent flow of stomach acids and like undesireable fluids from the stomach into the esophagus and into the trachea and lungs. Such a mixture of stomach acids and like fluids with the respiratory tract produces an undesireable "aspiration" which can complicate proper breathing of the patient.

Tracheal cuffs, per se, are known. Several tracheal tubes are on the market which in one way or another are provided with cuffs which attempt to properly seal the trachea between the trachael wall and the tracheal tube, thus only allowing the flow of air between the attached resuscitator and lungs. These prior art devices suffer from several inadequacies.

Prior art devices sometimes maintain a seal between the tracheal tube and the tracheal wall at all times. This is undesireable as it maintains an inadvertently high pressure against the trachea producing a "necrosis". Further, it has been found that when the pressure is high enough to perform the desired seal, there is an interruption of the blood circulation in the trachea tissue which can produce lesions upon the walls of the trachea.

Some prior art devices have attempted to solve this problem by periodically deflating the cuff in order to permit momentary circulation of blood through the tissues surrounding the cuff. This however, requires a highly skilled person who must no only perform the decompression of the cuff at the proper time, but at the proper pressure. If the deflation is excessive, the tracheal tube will not retain the proper seal and difficulty in the patient's breathing will result.

U.S. Pat. No. 3,769,983 issued to Abraham Merav and entitled "Medical Devices" provides a self-inflating tracheal tube which is of an "umbrella" fashion. The Merav device provides an open end which has an opening to the outer portion of the trachea between the tracheal tube and the cuff itself. This is undesireable, because the flow of mucous which normally proceeds in both directions up and down the tracheal wall can easily enter the cuff, filling it and halting its proper operation.

U.S. Pat. No. 3,616,799 issued to C. H. Sparks and entitled "Tubes with Sail Cuffs for Tracheal Intubation" provides such a similar umbrella type structure.

U.S. Pat. No. 3,709,227 issued to R. H. Hayward entitled "Endotracheal Tube with Positive Check Valve Air Seal" provides another umbrella type cuff which suffers from the aforementioned mucous accumulation and mucous build up problems.

While some patents have taught away from the use of an open ended or umbrella type cuff, they suffer from other problems which the prior art has failed to solve but which are solved by the present invention. U.S. Pat. No. 4,020,849 issued to R. R. Jackson and entitled "Cuff Inflation for Trachael Tubes" provides a cuff which has no openings between the cuff wall and endotracheal tube. Thus, it does not suffer from the problems of mucous accumulation as do the aforementioned patents. However, the Jackson patent provides a means for always retaining the cuff in an inflated position. This is undesireable, even though the cuff is inflated by air of the same pressure as is used to ventilate the lungs. At first, it will appear that such a device will never inflate to a pressure greater than the pressure of air used to fill the lungs of a patient during inhalation. However, if the patient were to cough or otherwise discharge an explosive force of air, air could enter the cuff and retain it thereafter in an overly inflated position for a time. Another U.S. Patent to R. R. Jackson entitled "Self-Inflating Endotracheal Tube" (U.S. Pat. No. 3,707,151) makes another attempt at solving the problems of reducing excessive pressure on the tracheal wall and stopping the flow of fluids from the stomach and esophagus into the lungs. In FIGS. 1 and 2 of U.S. Pat. No. 3,707,151, there is seen a self-inflating cuff which utilizes only the air flowing through the tracheal tube for its inflation. However, the Jackson device attempts to retain the cuff in an inflated position during exhalation of the patient. The '151 patent provides a check valve which seals the openings provided between the air conveying tube and the tracheal wall when air is being discharged from the trachea as is illustrated in FIG. 3 of U.S. Pat. No. 3,707,151.

These and other problems are discussed in an article appearing in "Annals of Surgery" Volume 184, No. 2, August 1976. In that article entitled "Tracheo-innominate Artery Erosion", the applicant of the present invention co-authors an article which analyzes the problem of tracheo-innomiate artery erosions.

The use of a check valve in order to seal the cuff in an inflated position during exhalation is dangerous since it allows excessive bursts of air to enter and be trapped within the cuff, the check valve closing with the high pressure air retained with no way for ventilation. Such could be the case, for example, if the patient were to cough expelling air from the lungs at increased pressures, pressures above the pressure of air being used to ventilate the patient.

Other attempts at the aforementioned problems which have perplexed the art but have yet been solved are further seen in other U.S. Patents, the following table of which is a listing. The following table provides a listing of some patents of which the applicant of the present invention is aware.

| PRIOR ART PATENTS | | |
|---|---|---|
| U.S. PAT. NO. | INVENTOR | ISSUE DATE |
| 3,481,339 | J. A. Millet Puig | Mar. 28, 1969 |
| 3,504,676 | V. N. F. Lomholt | June 13, 1967 |
| 3,616,799 | C. H. Sparks | Oct. 8, 1969 |
| 3,707,151 | R. R. Jackson | Dec. 26, 1972 |
| 3,709,227 | R. H. Hayward | Jan. 9, 1973 |
| 3,769,983 | A. D. Merav | Nov. 6, 1973 |
| 3,794,036 | R. G. Carroll | Feb. 26, 1974 |
| 4,020,849 | R. R. Jackson | May 3, 1977 |

3. General Discussion of the Present Invention

The present invention provides a device which solves all the prior art problems and shortcomings in a simple manner with a relatively inexpensive and uncomplicated structure. The device provides a cuff which self-inflates during inhalation of the patient using only the air that is used to ventilate the patient and using air at the same pressure. During exhalation of the patient, the cuff is promptly self-deflated, thereby removing pressure on the tracheal wall. Since the air utilized to inflate the lungs is likewise utilized to inflate the cuff, pressure on the trachea wall is sufficient but no grater than the pressure needed to form a substantially fluid tight seal with the trachea wall. During exhalation, a seal with the tracheal wall is not necessary,, as a seal is only necessary during inhalation of the patient. In order to solve the problem of the inadvertent travel of stomach acids and like undesireable fluids from the stomach and esophagus to the trachea and lungs, an obturator is provided for insertion above the implanatation point for the tracheal tube. The obturator provides the function of halting the flow of fluids in the trachea in a transverse direction.

The self-inflating and self-deflating feature of the cuff portion of the invention is provided by utilizing a valving means in the form of a path of lesser resistance of air into the tracheal cuff. It is desireable and it is provided with the present invention that air flow firstly into the tracheal cuff, (during inhalation) and firstly out of the tracheal cuff (during exhalations) by following a path of least resistance. In the preferred embodiment, the path of least resistance is provided in the form of an increased diameter opening between the tube wall and the tracheal cuff. Thus, the flow of air within the tracheal tube is firstly routed into the cuff before its travel in the tube itself. In the preferred embodiment a single opening is provided, however, a plurality of openings providing an overall lesser resistance for flow into the cuff rather than flow in the tube is of importance.

BRIEF DESCRIPTION OF THE DRAWINGS

For a further understanding of the nature and objects of the present invention, reference would be had to the following detailed description, taken in conjunction with the accompanying drawings, in which like parts are given like reference numerals and wherein:

FIG. 7 is a partial sectional view of the preferred embodiment of the apparatus of the present invention illustrating the adjustable flange portion thereof;

FIG. 7a is an enlarged schematic view of the adjustable flange portion of the preferred embodiment of the apparatus of the present invention illustrating the cam tip portion of the adjustable flange;

FIG. 8 is an enlarged perspective schematic view of the preferred embodiment of the apparatus of the present invention illustrating the operation of the cuff portion thereof during inhalation;

FIG. 9 is an enlarged schematic sectional view of the cuff portion of the preferred embodiment of the apparatus of the present invention illustrating operation of the cuff during exhalation; and FIG. 10 is a partial sectional view of the tube portion of an alternative embodiment of the apparatus of the present invention.

DETAILED DESCRIPTION OF THE PREFERRED EMBODIMENT

Figure 1:
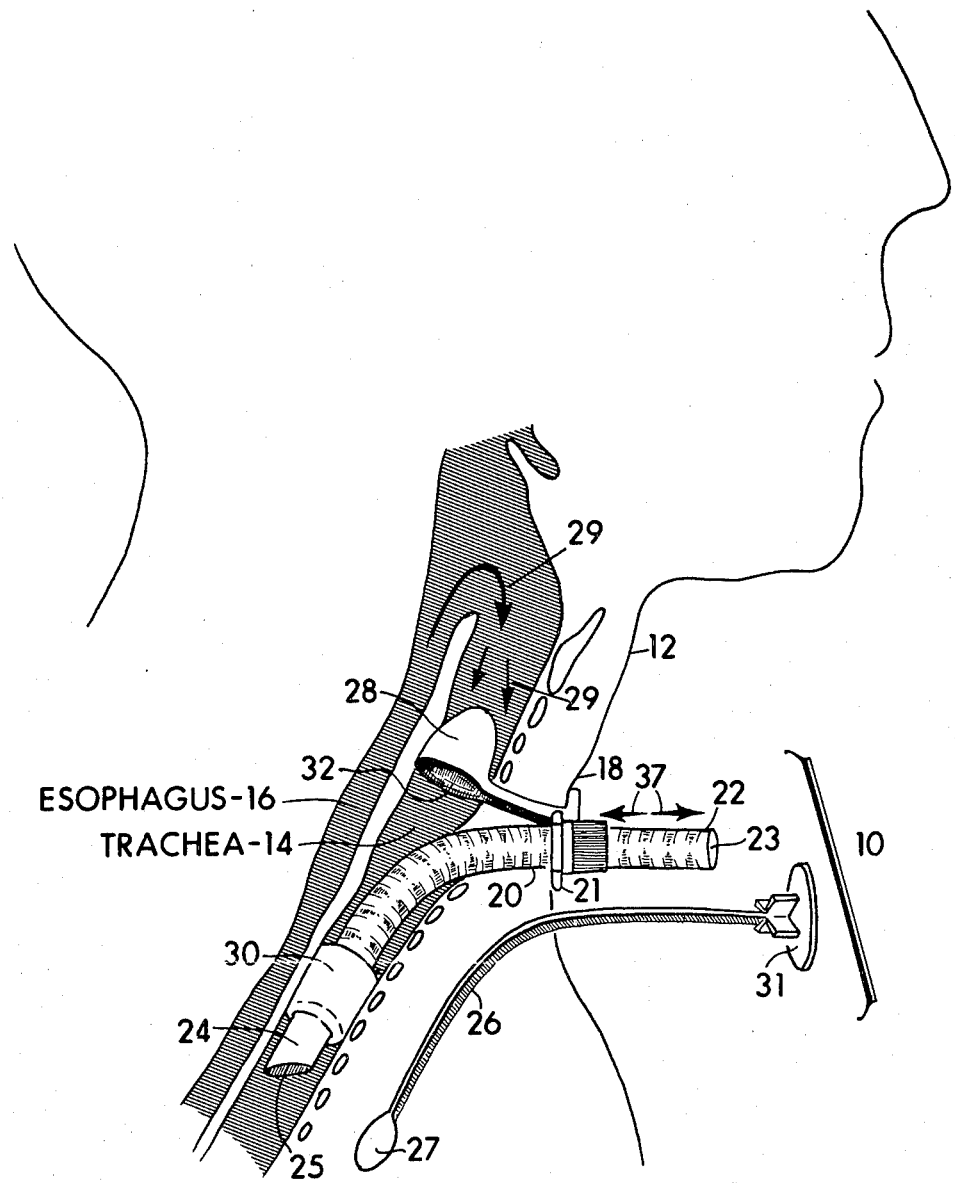
FIG. 1 is a perspective view of the preferred embodiment of the apparatus of the present invention illustrating its use as a tracheotomy tube.

FIG. 1 best illustrates the preferred embodiment of the apparatus 10 of the present invention.

In FIG. 1 there can be seen a schematic illustration of an individual 12 with the esophagus 16 and trachea 14 portions of the individual shown. The tracheal tube 10 can be seen inserted near the neck portion 18 of the patient 12 as is known in the art in an operation frequently performed by surgeons referred to as a tracheotomy.

Figure 3:
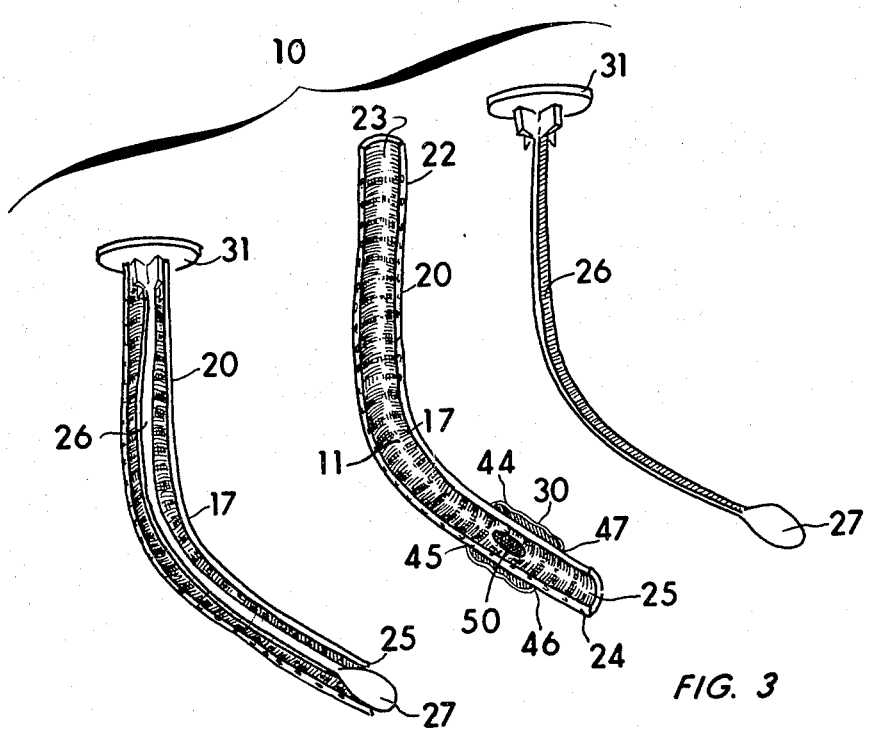
FIG. 3 is a sectional view of the preferred embodiment of the apparatus of the present invention illustrating the tube and cuff portions.

In FIG. 1, there can be seen an air conveying tube 20 having a proximal end portion 22 and a distal end portion 24. Note that an opening 23 is provided at the proximal end portion 22 of tube 20 with a corresponding opening 25 being provided at the distal end portion 24 of tube 20. Thus, an air conveying tube 20 is provided having an opening 23 for the entry of air into the tube "inner bore" for the conveying of air within tube 20 and an effluent opening 25 for discharge of air to the trachea and lungs. FIG. 3 best show the inner bore 11 provided to tube 20 for the conveying of air from inlet opening 23 to effluent opening 25.

A reinforcing guide member 26 is utilized to insert tube 20 into its proper position. The combination of guide 26 and tube 20 can best be seen in FIG. 3 when assembled for insertion. Note that tip 27 provides a closure to the opening 25 in tube 20 giving tube "body" for proper insertion by the surgeon.

In FIG. 1 there can be further seen obturator 28. Obturator 28 performs the function of stopping the undesireable flow of stomach acids and like undesireable fluids through esophagus 16 into trachea 14. The undesireable travel of such stomach acids and like fluids is illustrated schematically by the arrows 29 in FIG. 1. Note that obturator 28 is provided with a recessed or open end portion 32 which is sized to accomodate the finger tip of the surgeon thus facilitating easy insertion of the device into its proper position. A generally pointed tip 38 is provided on obturator 28 which aids in its insertion through openings in the neck and guides its placement into the trachea 14. In FIG. 1 the obturator is shown in its proper position aside tube 20 and blocking trachea 14. Obturator 20 would be sized of a diameter D (FIG. 2) as to substantially seal fluids in a transverse direction in the trachea.

In FIG. 1 there can further be seen a tracheal cuff 30. Tracheal cuffs 30 are known, and are used to seal trachea 14, with cuff 30 inflating and abutting the tracheal wall as is best seen in FIG. 1. During inspiration (as will be described more fully hereinafter) the tracheal cuff 30 inflates and seals the tracheal wall disallowing the escape of air in a direction through the trachea away from the lungs thereby forcing and channeling the flow of air, oxygen or similar desirable gas through the trachea to inflate the lungs as is desirable. Cuff 30 can be manufactured of a thin flexible film material such as polypropylene, polyethylene, PVC or like substantially fluid impermeable plastic film materials.

Flange 21 is shown in FIG. 1 and is attached to tube 20. Flange 21 provides a seat or point of anchoring for the entire tracheal tube 10 in its proper location at the neck portion 18 of the patient 12. As will be described more fully hereinafter the flange 21 as is provided in the preferred embodiment of the apparatus of the present invention is adjustable with respect to tube 20. This adjustability is illustrated schematically by arrows 37 in FIG. 1.

Figure 4:
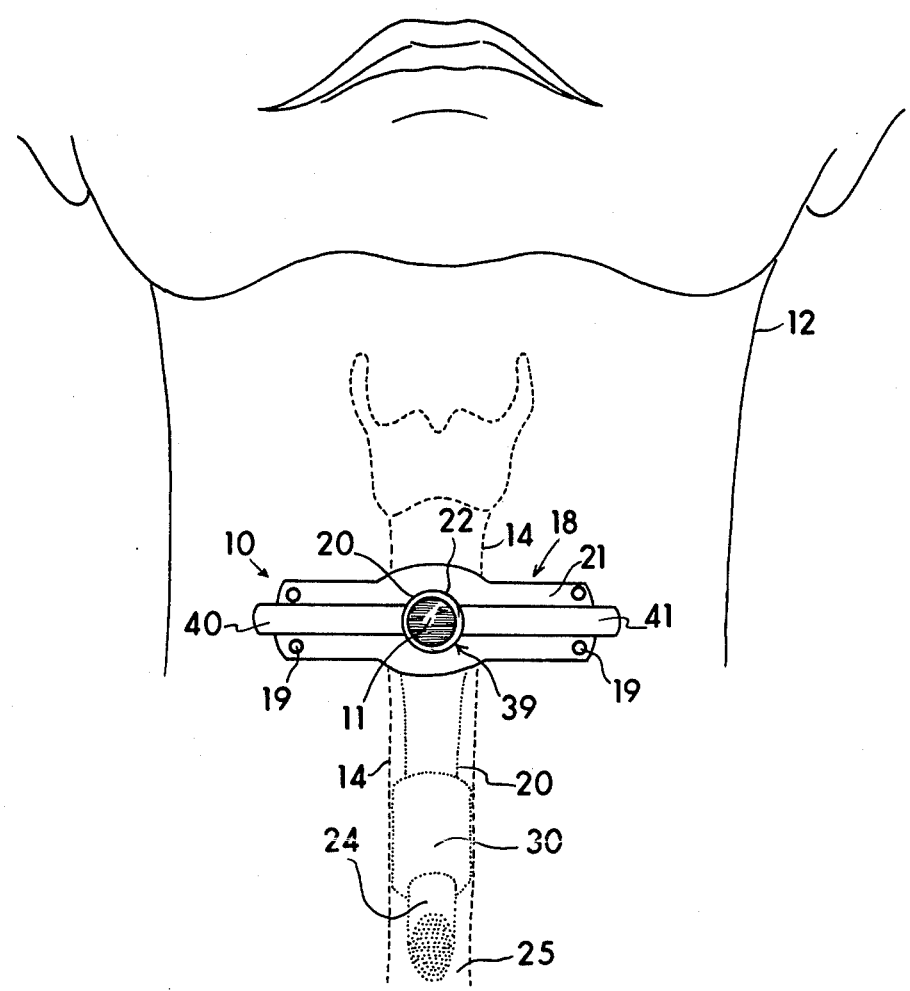
FIG. 4 is a schematic plan view of the preferred embodiment of the apparatus of the present invention illustrating its use as a tracheotomy tube.

FIG. 4 illustrates a plan view of the preferred embodiment of the apparatus 10 of the present invention illustrating more particularly the construction of flange 21. Note in FIG. 4 that flange 21 sits atop the surface neck portion 18 of the patient 12 with the air conveying tube 20 descending downwardly through the skin and underlying portions of the neck 18 area into the trachea 14 as was seen illustrated in FIG. 1. In FIG. 4, it can be seen that flange 21 surrounds and supports the proximal end portion 22 of tube 20. An opening 39 is provided in flange 21 through which tube 20 is attached to flange 21. A supportive collar 43 can be provided if desired. The opening 39 in flange 21 would be of an identical or slighly larger diameter than the outer diameter of the tube 20. A plurality of openings 19 are provided in flange 21 which openings allow the attachment of a suitable tie member such as an umbilical tape for the attachment of flange 21 about the neck portion 18 of the patient 12 anchoring flange 21 and tube 10 in a stable position. A pair of pivotable clamps 40, 41 can also be seen in FIG. 4 which clamps 40, 41 provide an adjustability of flange 40 with respect to tube 20 as will be described more fully hereinafter and is more particularly illustrated in FIGS. 2, 7 and 7A.

Figure 2:
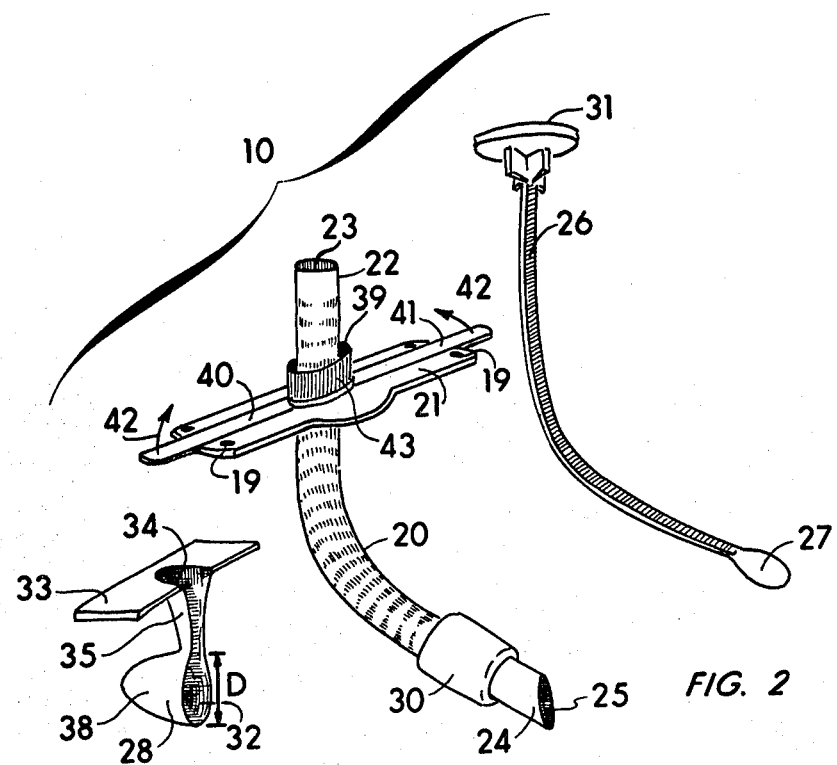
FIG. 2 is a perspective exploded view of the preferred embodiment of the apparatus of the present invention.

FIGS. 2 and 3 illustrate more particularly the construction of the preferred embodiment of the apparatus 10 of the present invention. In FIG. 2, there is shown reinforcing guide 26 with its enlarged tip portion 27 and cap 31 as was discussed previously in connection with FIG. 1. Note that obturator 28 is more particularly shown in FIG. 2. Obturator 28 is provided with an upper yoke 34 with a lower depending connective portion 35 attaching yoke 33 to obturator 28. The diameter "D" of obturator 28 is schematically illustrated in FIG. 2. Note that a recess 34 is provided to obturator 28 which recess registers with and abutts tube 20 during operation of the apparatus 10. In a normal operation, obturator 28 would first be inserted into position through an opening formed by the surgeon. Thereafer, tube 20 would easily be insertable into the formal opening since recess 34 of obturator 28 would not block or otherwise hinder insertion of tube 20 into its proper position as is illustrated in FIG. 1. Recess 34 and open end portion 32 of obturator 28 can be sized to accomodate a finger of the surgeon, providing a gripping surface to allow easy insertion of obturator 28 into its operating position within trachea 14 (See FIG. 1).

The adjustability of flange 21 with respect to tube 20 is schematically illustrated by the arrows in FIG. 2. Curved arrows 42 further illustrate the adjustability by showing the pivotal movement of pivotal clamps 40, 41. As can best be seen in FIG. 7, clamps 40, 41 operate from a first flush "operative" position with respect to flange 21 to a second raised "adjustment" position (the "adjustment" position shown in phantom lines in FIG. 7). The second or "adjustment" position allows flange 21 to be moved in a direction co-linear with the bore 11 of tube 20. This allows the surgeon to properly "fit" tube 20 with respect to the needs of a particular patient, thereby putting minimal stress on the tracheal wall which commonly occurs with prior art type tubes due to an improper fit. Turning now to FIGS. 7 and 7A, it can be seen that each pivotal clamp 40, 41 is provided with a pivot 54 and a cam tip portion 60, 61. Notice that the cam tip portions 60, 61 abut and frictionally engage the wall 17 of tube 20 when clamps 40, 41 are in their normal "flush" or "operative" position. Cam tips 60, 61 can be provided with serrated teeth 72, if desireable (See FIG. 7A) to enhance their gripping ability against the wall portion 17 of tube 20. During normal operation, pivotal clamps 40, 41 as aforementioned, will assume a flush "operative" position as is shown in FIG. 2. Clamps 40, 41 can be secured in this flush position by using adhesive tape, or by providing locking tabs on flange 21.

Figure 5:
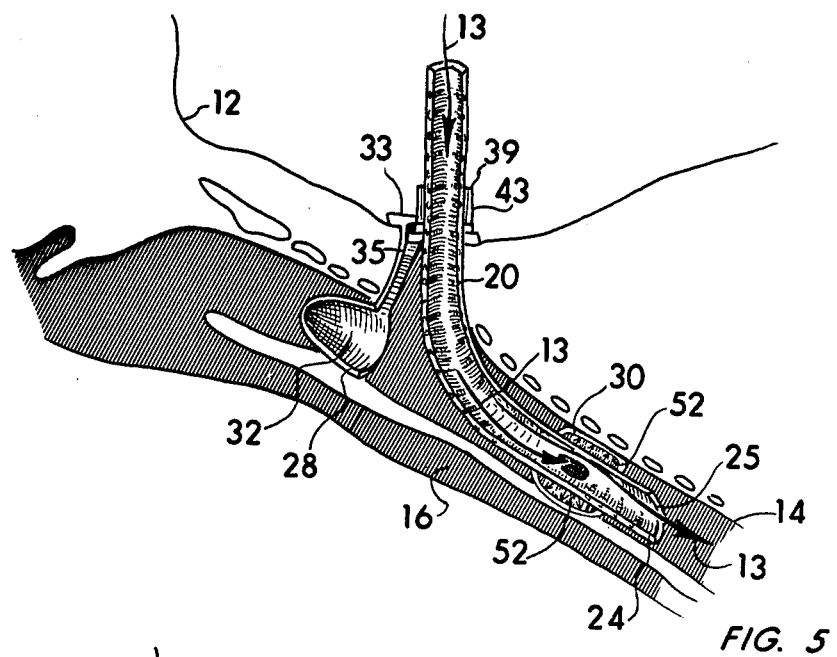
FIG. 5 is a sectional view of the preferred embodiment of the apparatus of the present invention illustrating its use as a tracheotomy tube, the illustration showing operation during inhalation.
Figure 6:
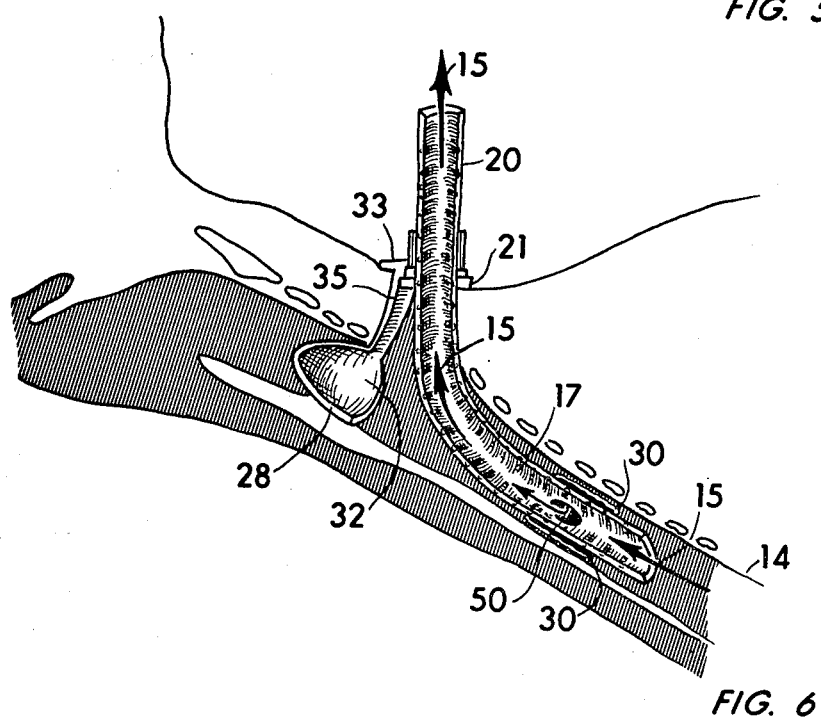
FIG. 6 is a sectional view of the preferred embodiment of the apparatus of the present invention illustrating its use as a tracheotomy tube, the illustration showing operation during exhalation.

FIGS. 3, 5 and 6 are sectional views showing the inner portion of tube 20, obturator 28, and cuff 30. FIGS. 3, 5, and 6 thus illustrate with particularity the flow of air during both inhalation and exhalation. In FIG. 5, arrow 13 schematically represents the flow of inward air during inhalation of the patient 12. Such inhalation could be produced by any of a variety of known resuscitators or like medical appliances presently known to supply air to the patient through tube 20. In FIG. 5 note that arrows 52 schematically illustrate the flow of air through tube 20 into cuff 30 by way of opening 50. Note that cuff 30 will self-inflate during inhalation of the patient thus forming a seal with cuff 30 against the wall portion of the trachea 14 as is desirable.

Conversely, the cuff will deflate as is best seen in FIGS. 6 and 9 during exhalation of the patient 12. Arrows 15 in FIG. 6 schematically illustrate the flow of air during exhalation of the patient 12. Note that cuff 30 has assumed a deflated position not in contact with the walls of the trachea 14.

From an inspection of FIGS. 3, 5, 6, and 7–9, it can be seen that the only communication of a source of air to cuff 30 is by means of opening 50. Opening 50 would preferably be at least one opening, but a plurality of openings would be suitable. Openings 50 would preferably provide lesser resistance for air flow through tube 20 than the resistance for air flow through tube 20 than the resistance provided to the flow of air by exit opening 25. This lesser resistance could be in the form of an increased diameter of the openings 50 into cuff 30. The diameter of tube bore 11 having a smaller diameter than the diameter of cuff opening 50 thus provides a greater resistance to air flow within tube bore 11. This is important, since such a difference in resistances of the flow of air into the cuff 30 as opposed to the flow of air into trachea 14 at the distal end portion 24 of tube 20 produces a "valving" effect which will urge air firstly to cuff 30 and inflate it before in fact air flows into the trachea and adjacent lungs during inhalation. Though the difference in timing will be minute, the difference in resistance will (as will be apparent to one skilled in the art) inflate cuff 30 firstly. In a like manner, the difference in resistances of openings 50 and tube bore 11 diameter will cause cuff 30 to promptly deflate as is desireable upon the institution of exhalation of the patient. Note that the cuff is promptly deflated during exhalation rather than being retained inflated by chek valves or similar structures as are prior art tubes. The chance of excess pressure (due to trapped air generated by coughing, for example) against the trachea is minimized.

Thus, the present invention teaches a tracheal tube apparatus 10 which inflates the cuff to a pressure substantially identical with the pressure being supplied to the lungs, and promptly deflates the cuff during exhalation of the patient, negating the aforementioned problems of constant and/or excessive pressure against the trachea 14.

With the increased diameter of opening 50 providing a lesser resistance for the flow of air through tube 20 to cuff 30, there is no chance for the trappage of higher pressures of air in cuff 30 as can be the case with prior art devices which attempt to keep the cuff in an inflated position at all times. The present invention negates the problems of excessive pressure on the trachea 14 which problem several prior art devices have theretofore attempted but failed to solve.

Since obturator 28 is provided to shut off the flow of air as well as the flow of fluids in trachea 14, there is no need to retain cuff 30 in an inflated position as is the case with prior art devices. It can be appreciated by one skilled in the art that the pressure in cuff 30 will always be substantially identical to the pressure in trachea 14 at the distal end portion 24 of tube 20. The substantially identical pressures will negate the change for leakage between the seal formed by the cuff wall 36 against the trachea 14 as best can be seen in FIG. 8.

FIG. 9 illustrates collapsed condition of cuff 30 during exhalation, with no pressure of the cuff seen against the trachea wall as is desireable.

FIG. 10 shows a section view of a portion of tube 20 illustrating the construction thereof. FIG. 10 represents an alternative embodiment to the construction of tube 20 and the tube wall 17. A spiral reinforcing element 70 is provided in a normally flexible tube wall 17. The lumen of the tube is not lost, though its flexibility is greatly enhanced over prior art tubes which are of a "stiff" nature in order to retain the necessary structural integrity to resist deformation of the tube lumen. The flexible tube 20 shown in FIG. 10 reduces pressure of the tube (especially by its distal end portion 24) against trachea 14.

Because many varying and different embodiments may be made within the scope of the inventive concept herein taught, and because many modifications may be made in the embodiments herein detailed in accordance with the descriptive requirements of the law, it is to be understood that the details herein are to be interpreted as illustrative and not in a limiting sense.

What is claimed as invention is:

1. A self-inflating and self-deflating tracheal tube apparatus comprising:
   a. an elongated hollow tube, said tube having a proximal opening and a distal opening, there being provided a central air conveying bore of uniform unconstricted diameter through said tube from said proximal opening to said distal opening;
   b. an inflatable cuff of generally tubular configuration, said cuff having a diameter larger than the diameter of the trachea into which the tube is inserted, said cuff being of a substantially thin flexible film material and further being secured to said tube adjacent the distal end thereof, said cuff being substantially sealed in a fluid-tight fashion to said tube; and
   c. air flow control means cooperatively connecting said air conveying bore and said cuff for controlling the flow of air from said bore into said cuff, said means providing a lesser resistance to air flow into said cuff than the resistance of air flow within said air conveying bore, said control means comprising at least one opening connecting said bore and said cuff, said opening having a larger cross sectional area than the cross sectional area of said bore, the flow of air in said tube from said proximal opening to said distal opening so controlled producing a preferred inflation of said cuff, the flow of air in said tube from said distal end to said proximal end causing said cuff to collapse; and
   d. means fittable against said tube for restricting the flow of fluids within the trachea, a portion of said means placeable within the trachea above the point of placement of said elongated flexible hollow tube.

2. The tracheal tube of claim 1 wherein said restricting means is an obturator having a diameter substantially identical with the diameter of the trachea into which it is placeable.

3. The tracheal tube of claim 2 wherein said obturator is provided with means for gripping said obturator, said gripping means comprising a recess on said obturator, a portion of said recess fittable against said hollow tube.

4. The tracheal tube of claim 3 wherein said obturator is further provided with an upper yoke portion, said yoke portion abuttable against said hollow tube, a portion of said yoke providing a flange abuttable against the neck portion of the patient to which the tracheal tube is attached.

5. The tracheal tube of claim 1 further comprising a flange attachable to said tube, said flange being adjustable on said tube in a direction substantially colinear with the inner bore of said tube.

6. The tracheal tube of claim 5 further comprising gripping means on said flange for affixing said flange on said tube in a substantially rigid attachment therewith.

7. The tracheal tube of claim 6 wherein said gripping means is comprised of a movable clamp on said flange.

8. The tracheal tube of claim 7 wherein said movable clamp is comprised of a pair of pivotal clamps, each of said pivotal clamps being provided with a cam tip portion, said cam tip portion frictionally engaging said tube once said pivotal clamps assume a flush operative position substantially adjacent of said flange.

9. The tracheal tube of claim 8 wherein said cam tip portion of said pivotal clamps is provided with gripping teeth, said teeth frictionally engaging said tube once said pivotal clamp assumes a flush operative position.

10. The tracheal tube of claim 1 wherein said tube is flexible about its longitudinal axis, there being further provided reinforcement means in the wall portion of said tube for retaining the lumen of said tube.

11. The tracheal tube of claim 10 wherein said reinforcement means is a spiral reinforcing element in said flexible tube wall.

12. An adjustable tracheostomy tube comprising:
   a. an elongated hollow tracheostomy tube, said tube having a proximal opening, and a distal opening, there being provided a central air conveying bore through said tube connecting said proximal opening and said distal opening said tube passing during operation through a surgically formed opening in the neck of a patient;
   b. an inflatable cuff on the generally distal end portion of said tube, said cuff being inflatable to form a substantially air tight seal with the tracheal wall;
   c. adjustable neck flange means movably connected to said tube for securing said tube to the neck of a patient during a tracheostomy, said neck flange means being adapted for gripping attachment to said tube at intervals along its length.

13. The tracheostomy tube of claim 12 wherein said cuff is inflatable with a flow of air through said bore from said proximal opening to said distal opening.

14. The tracheostomy tube of claim 12 wherein said adjustable means is movable on said tube along the length thereof.

15. The tracheostomy tube of claim 12 wherein said adjustable means is a flange movably attached to said tube.

16. The tracheostomy tube of claim 15 wherein said flange is provided with a tube opening therethrough and said tube is movably fitable to said flange through said tube opening.

17. The tracheostomy tube of claim 16 further comprising means associated with said flange for affixing said flange to said tube at a desired operative position on said tube.

18. The tracheostomy tube of claim 17 wherein said affixing means is at least one clamp.

19. The tracheostomy tube of claim 18 wherein said clamp is pivotally mounted on said flange and said clamp is provided with a tip portion being capable of securedly gripping said tube.

20. The tracheostomy tube of claim 20 wherein said clamp is movable from a first adjustable position to a second operative position, said first adjustable position allowing said tube, to move with respect to said flange, said second operative position affixing said flange to said tube in a fixed substantially rigid connection with said tube.

21. The tracheostomy tube of claim 20 wherein said clamp is provided with a tip portion being capable of securedly gripping said tube, said tip portion frictionally engaging said tube when said clamp is in said second operative position, movement of said clamp to said first adjustable position removing said tip portion from frictional engagement with said tube.

22. The tracheostomy tube of claim 21 wherein said tip portion is provided with a plurality of serrated teeth.

23. The tracheostomy tube of claim 19 wherein a plurality of said clamps are provided on said flange.

24. The tracheostomy tube of claim 21 wherein a plurality of said clamps are provided on said flange.

25. An adjustable tracheostomy tube comprising:
   a. an elongated flexible hollow tracheostomy tube, said tube having a proximal opening, and a distal opening, there being provided a central air conveying bore through said tube connecting said proximal opening and said distal opening, said tube passing during operation through a surgically formed opening in the neck of a patient, said tube being flexible with respect to the axis of said air conveying bore;
   b. an inflatable cuff on the generally distal end portion of said tube, said cuff being inflatable to form a substantial air tight seal with the tracheal wall of the patient;
   c. adjustable neck flange means movably connected to said tube for securing said tube to neck of a patient during a tracheostomy, said neck flange means being adapted for gripping attachment to said tube at intervals along its length; and
   d. reinforcement means connected to said flexible tube for retaining the lumen of said flexible tube.

26. The flexible tracheostomy tube of claim 25 wherein said reinforcement means is a spiral reinforcing member associated with said tube wall.

27. The flexible tracheostomy tube of claim 26 wherein said spiral reinforcing member is mounted within said tube in the tube wall.

28. The flexible tracheostomy tube of claim 27 further comprising a guide member insertable into the bore of said tube for retaining said tube in a substantially rigid form said rigid form allowing insertion of said tube into the opening in the neck of a patient during a tracheotomy.

29. A self-inflating, self-deflating adjustable tracheal tube comprising:
   a. an elongated flexible hollow tube, said tube having a proximal opening and a distal opening therein, there being further provided an air conveying bore in said tube for conveying air from said proximal opening to said distal opening;
   b. an inflatable cuff of generally tubular configuration attached to the distal end portion of said tube, said cuff having a diameter larger than the diameter of the trachea into which said tube is inserted, said cuff being of a substantially thin flexible film material and further being secured to said tube adjacent the distal end thereof, said cuff being sealed at its edges in a substantially air tight fashion to said tube, there being further provided at least one opening connecting said bore and said cuff, said opening having a larger cross sectional area than the cross sectional area of said bore, the flow of air in said tube from said proximal opening to said distal opening producing an inflation of said cuff, the flow of air in said tube from said distal end to said proximal end causing said cuff to collapse;
c. a flange movably mounted on said tube for securing said tube to the neck of a patient into which said tube is inserted during a tracheotomy said flange having a flange opening therein, said opening having a diameter at least as great as the external diameter of said tube, said tube movably attached to said flange through said flange opening;
d. at least on clamp movably mounted on said flange, said clamps being capable of grippingly engaging said tube; and
e. an obturator fittable against said tube, said obturator sized to fit within the trachea of a patient in a fluid sealing position which retards the flow of fluids in a transverse direction of the trachea, said obturator comprising:
an obturator body having a smaller pointed tip portion and a larger trachea sealing portion,
an obturator yoke fittable against the neck of a patient and connectably fittable against said tube; and
a connective portion joining said obturator body and said yoke.

30. The tracheal tube of claim 29 wherein said obturator yoke and said connective portion are each provided with a recess allowing said yoke and said connective portion to fit against and register with said tube.

31. The tracheal tube of claim 30 wherein said tube is flexible, being arcuately adjustable about its longitudinal axis and there is further provided means for reinforcing said tube wall, said reinforcing means retaining the lumen of said tube.

32. The tracheal tube of claim 31 further comprising a reinforcing guide member insertable into the bore of said tube for retaining said tube in a substantially rigid form, said rigid form giving said tube body allowing insertion of said tube into the opening in the neck of a patient during a tracheotomy.

* * * * *